United States Patent
Bressanutti et al.

(10) Patent No.: US 10,078,948 B2
(45) Date of Patent: Sep. 18, 2018

(54) SMOKE DETECTOR WITH A DOUBLE OPTICAL CHAMBER

(71) Applicant: Honeywell International Inc., Morristown, NJ (US)

(72) Inventors: Massimo Bressanutti, Sesto al Reghena (IT); Andrea Frison, Monfalcone (IT)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 15/006,701

(22) Filed: Jan. 26, 2016

(65) Prior Publication Data
US 2017/0213434 A1 Jul. 27, 2017

(51) Int. Cl.
G01N 21/00 (2006.01)
G08B 17/113 (2006.01)
G01N 21/53 (2006.01)

(52) U.S. Cl.
CPC .......... *G08B 17/113* (2013.01); *G01N 21/53* (2013.01)

(58) Field of Classification Search
CPC ... G08B 17/107; G08B 17/113; G01J 5/0014; G01M 15/10; G01N 21/53
USPC ......... 356/432–440, 337–338; 250/574, 576; 340/514, 945, 630
See application file for complete search history.

(56) References Cited

U.S. PATENT DOCUMENTS

| | | | |
|---|---|---|---|
| 3,885,162 A * | 5/1975 | Geertz | G01N 21/534 250/216 |
| 3,968,379 A | 7/1976 | Crane | |
| 4,121,110 A * | 10/1978 | Solomon | G08B 17/113 250/574 |
| 4,583,859 A * | 4/1986 | Hall, II | B01D 46/46 250/236 |
| 4,680,576 A * | 7/1987 | Bauer | G08B 17/113 250/573 |
| 4,870,394 A | 9/1989 | Corl et al. | |
| 5,351,034 A * | 9/1994 | Berger | G08B 17/107 250/389 |
| 6,914,535 B2 * | 7/2005 | Matsukuma | G08B 17/113 340/577 |
| 7,872,815 B2 | 1/2011 | Sonderegger et al. | |
| 8,899,097 B2 * | 12/2014 | Wu | G01N 21/534 73/28.01 |
| 9,196,141 B1 * | 11/2015 | Schmidt | G08B 29/185 |

(Continued)

OTHER PUBLICATIONS

System Sensor® Series 200 Advanced—Photoelectric Smoke Detector, Model 22051E, Copyright © 2009 System Sensor.
(Continued)

*Primary Examiner* — Hoa Pham
(74) *Attorney, Agent, or Firm* — Husch Blackwell LLP (57) ABSTRACT

A smoke detector with an improved double optical chamber is provided. The smoke detector can include a chamber cover, a chamber base, an optical block, and a printed circuit board, wherein a smoke chamber is bound by the chamber cover, the chamber base, and the optical block, wherein a monitoring chamber is bound by the chamber base, the optical block, and the printed circuit board, wherein the monitoring chamber is closed to access outside of the smoke detector, and wherein radiation from only the monitoring chamber produces a non-zero clean air value of the detector.

19 Claims, 6 Drawing Sheets

(56) References Cited

U.S. PATENT DOCUMENTS

2015/0204781 A1* 7/2015 Wagner ............... G08B 17/107
356/342
2015/0379846 A1 12/2015 Bressanutti et al.

OTHER PUBLICATIONS

System Sensor® Series 200 Advanced—Photoelectric Smoke / Thermal Multi-Criteria Fire Detector, Model 22051TE, Copyright © 2009 System Sensor.
OSRAM Opto Semiconductors—Reflective Interrupter, Version 1.0 (customer specific / Pittway), SFH 7781, Jun. 23, 2015.

* cited by examiner

FIG. 6

SMOKE DETECTOR WITH A DOUBLE OPTICAL CHAMBER

FIELD

The present invention relates generally to smoke detectors. More particularly, the present invention relates to a smoke detector with a double optical chamber.

BACKGROUND

Point smoke detectors that use scattered light, that is, photoelectric detectors, are known in the art. For example, known photoelectric detectors include a sensing chamber into which smoke enters, an optical system to generate a flash of light and detect the light scattered by smoke particulate, and an electronic system to process and transmit a signal proportional to the smoke. The optical system includes an emitter and a receiver that are located in such a way so that a high amount of the light projected by the emitter is collected by the receiver only in the presence of the smoke when the smoke particulate scatters the light.

In known photoelectric detectors, smoke detection based on optical scattering is affected by inaccuracy sources other than the smoke that cause the light to scatter. For example, known inaccuracy sources include, but are not limited to (1) dust accumulation on sensing chamber surfaces that cause a slow output signal drift and an increase in smoke sensitivity, (2) small objects or insects that settle on walls of the sensing chamber and that cause quick output signal variations and false alarms, (3) moisture and steam effects that cause unwanted deviations of light radiation, false alarms and signal faults, and (4) temperature variations that cause emitter and receiver characteristic changes.

Although a high amount of the light projected by the emitter is collected by the receiver only in the presence of the smoke, a small amount of the light projected by the emitter is also collected by the receiver even in the absence of the smoke. In this manner, a low level output signal or a clean air value is generated. It is known to use the clean air value to monitor the correct operating conditions of the emitter and the receiver and to easily and quickly calibrate a detector in a factory.

The clean air value of an output signal is typically generated by the light from the emitter being reflected multiple times within the sensing chamber. Accordingly, the clean air value typically has depended on the geometrical configuration, roughness, and color of the sensing chamber. However, when the light reflects multiple times within the sensing chamber, the clean air value of the output signal is more sensitive to the inaccuracy sources described above so unwanted signal variations, false alarms, and sensitivity variations occur more easily.

The above-identified disadvantages can be minimized when the sensing chamber is designed so that the clean air value is zero. However, such designs introduce more costs to calibrate the detectors.

Accordingly, some photoelectric detectors have been designed to include two optical chambers, and U.S. Pat. No. 3,968,379, U.S. Pat. No. 7,872,815, and U.S. Pat. No. 4,870,394 disclose examples of such detectors. However, each of these detectors includes a second receiver, for example, a reference receiver, in addition to a smoke receiver that is illuminated by part of emitter radiation in a compensating or reference chamber. These two receivers are connected in a bridge circuit and an electrical signal output from the bridge circuit is used to generate an alarm signal.

Accordingly, the smoke receiver is not directly monitored. Furthermore, because two receivers are required, these types of detectors require more opto-electronic and electronic components and therefore, are more expensive to manufacture and implement.

The goal of any double chamber scheme is to reduce clean air signal drift due to dust and dirt accumulating during the detector's lifetime. However, it is preferred that any double chamber scheme includes an effective configuration that is low cost to manufacture and implement. This is particularly so in two cases: (1) when a smoke detector is in an environment where a standard photoelectric smoke detector gets dirty quickly and (2) when a smoke detector includes a high sensitivity or high gain photoelectric detector.

In view of the above, there is a continuing, ongoing need for a smoke detector with an improved double optical chamber.

DETAILED DESCRIPTION

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments disclosed herein can include a smoke detector with an improved double optical chamber. In accordance with disclosed embodiments, the double optical chamber as disclosed herein can be assembled and included in any smoke detector that implements photoelectric detection. Advantageously, the double optical chamber as disclosed herein can reduce the need for maintenance of standard photoelectric detectors, especially in dusty environments or in environments polluted by insects while also providing a simple and cost-effective opto-mechanical configuration and implementation for high sensitivity photoelectric detectors and such detectors in aspirating systems. Furthermore, the double optical chamber as disclosed herein can reduce clean air drift due to dust, humidity, and other small objects entering a smoke chamber while easily and quickly calibrating and monitoring the correct operation of an emitter and a receiver of the detector.

In some embodiments, the double optical chamber as disclosed herein can include two different chambers: the smoke chamber and a monitoring chamber. Both chambers can be illuminated by the same emitter, and light can be collected by the same receiver so that only two opto-electronic devices are needed to implement the double optical chamber. Such an implementation can keep the cost of the configuration low.

In the smoke chamber, the light from the emitter can be scattered by smoke particles onto the receiver, thereby generating an output signal. The geometrical configuration of the smoke chamber can be such that, using only this chamber, a zero clean air value can be obtained. Accordingly, the contribution to signal drift due to the dust and the humidity can be minimized, thereby reducing maintenance needs. In some embodiments, the smoke chamber as disclosed herein can reduce or eliminate multiple reflections within the smoke chamber. Advantageously, this results in a reduction of false alarms and in a very low drift due to progressive chamber dirtiness, for example, from dust accumulation, that can cause output signal saturation.

The monitoring chamber may not have access from outside of the smoke detector. Accordingly, in some embodiments, smoke, the dust, and other objects cannot enter the monitoring chamber. However, in the monitoring chamber, a sufficient amount of the light from the emitter can be projected onto the receiver to obtain a significant and useful clean air value that can be used to calibrate the detector and monitor, in a reliable and cost effective way, the correct operation of the emitter and the receiver during the lifetime of the detector. Indeed, because the above-identified noise sources can be kept out of the monitoring chamber, in some embodiments, the clean air value is not affected by these noises.

In some embodiments, the double optical chamber as disclosed herein can include a light splitter optical block, a chamber cover, and a chamber base, and these three parts can form the smoke and monitoring chambers as described above and herein. For example, the smoke chamber into which the smoke can enter can be delimited at the top by the chamber cover and at the bottom by the light splitter optical block and the chamber base. The monitoring chamber into which the smoke cannot enter and does not have the access from outside of the detector can be delimited at the top by the light splitter optical block and the chamber base and at the bottom by a printed circuit board (PCB).

The light splitter optical block as disclosed herein can be both a light splitter and a light collector. For example, the optical block can divide light radiation from the emitter into two beams: a sensing beam and a monitoring beam. In some embodiments, the sensing beam can be more intense than the monitoring beam. The sensing beam can be projected into the smoke chamber to sense the smoke during fire. For example, this radiation can come from a main radiation cone of the emitter, and the light scattered by the smoke particles in the smoke chamber can be collected by a main view cone of the receiver. Conversely, the monitoring beam can be projected into the monitoring chamber to calibrate the detector and monitor the correct operation of the emitter and the detector. For example, this radiation can come from secondary lobes of the emitter through a first hole in a bottom surface of an emitter housing formed in the optical block. A similar and corresponding second hole can be disposed in a receiver housing formed in the optical block for capturing the light reflected in the monitoring chamber, and the light collected by the receiver from the monitoring chamber can be used to generate a non-zero clean air value.

In some embodiments, the first hole in the emitter housing and the second hole in the receiver housing can be small and circular, rectangular, or any other shape as would be desired by one of ordinary skill in the art. For example, in circular embodiments, each of the holes can have a diameter between 1.5 mm and 3 mm, for example, on the order of 2 mm. In square or rectangular embodiments, each of the holes can have an area between 2 $mm^2$ and 8 $mm^2$. In some embodiments, the first and second holes can be identical or can have different sizes or shapes. However, in some embodiments, the size of each of the holes can be related to emitter light flux, the receiver's sensitivity, and reflectivity surfaces of the monitoring chamber.

In some embodiments, the area and placement of the first and second holes can be critical to proper operation of the double optical chamber. For example, in some embodiments, each of the holes can be placed below their respective optical device in such a way as to be fully covered by the respective optical device and so that the monitoring chamber remains closed. Furthermore, in some embodiments, each of the holes can be wide enough to collect a sufficient, proper, and necessary amount of radiation.

As described above, the first hole—the emitter hole—can capture the radiation from the emitter and illuminate the monitoring chamber. The second hole—the receiver hole—can collect the radiation from the monitoring chamber and illuminate the receiver, which can generate, with a related current amplifier, a suitable clean air value. For example, in known detectors that include a zero clean air chamber cover, operation with a known optical block can result in the clean air value on the order of 40 mV. However, in detectors that include the zero clean air chamber cover, operation with the light splitter optical block as disclosed herein can result in the clean air value on the order of 855 mV. From this illustrative example, it can be understood that embodiments disclosed herein advantageously result in an improved clean air value.

It is to be understood that the double optical chamber as disclosed herein can be included in known and existing smoke detectors. For example, such smoke detectors can be retrofitted to include the double optical chamber as disclosed herein, but without further modification of the detector's firmware and hardware. Indeed, in some embodiments, the double optical chamber as disclosed herein can employ the same optical and electronic devices of known smoke detectors. For example, the detector that includes the double optical chamber as disclosed herein can be calibrated as is known in the art except that the clean air value can be generated from the radiation received only from the monitoring chamber of the double optical chamber as disclosed herein.

Figure 1:
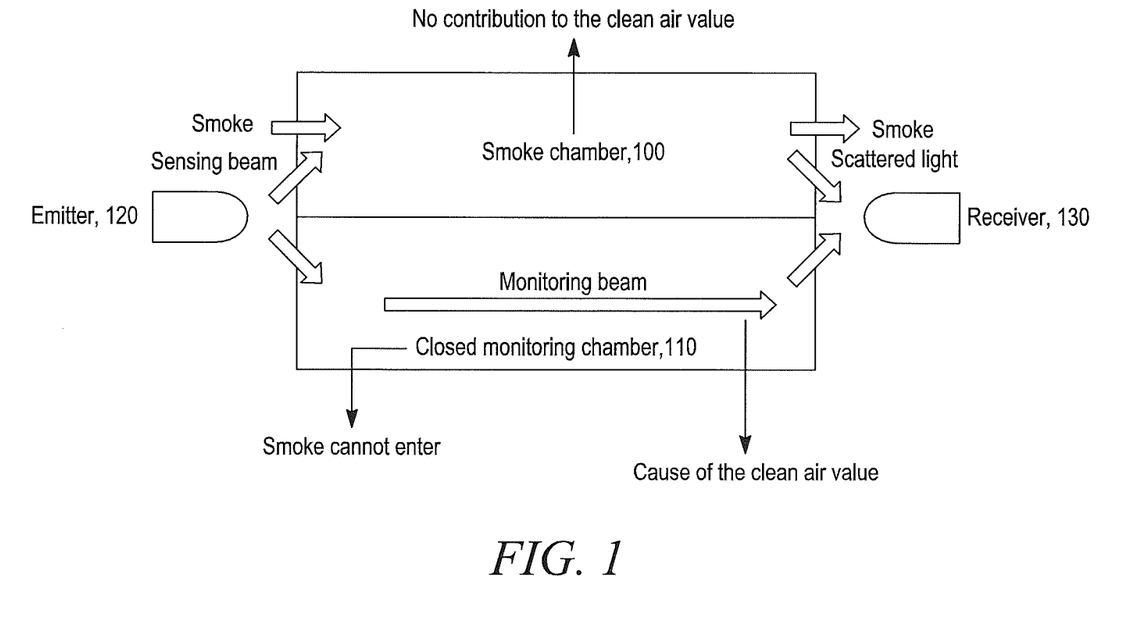
FIG. 1 is a block diagram of a smoke detector with a double optical chamber in accordance with disclosed embodiments.

FIG. 1 is a block diagram of a smoke detector with a double chamber in accordance with disclosed embodiments. As seen in FIG. 1, the double chamber can include a smoke chamber 100 and a monitoring chamber 110. A single emitter 120 can emit a sensing beam that is directed into the smoke chamber 100 and a monitoring beam that is directed into the monitoring chamber 110. Smoke can enter and pass through the smoke chamber 100, thereby causing the sensing beam to scatter, and scattered light can be received by the single receiver 130. However, it is to be understood that radiation received by the receiver 130 from the smoke chamber 100 has no contribution to a clean air value of the detector. The monitoring chamber 110 can be closed so that the smoke cannot enter the monitoring chamber 110, but the monitoring beam can pass through the monitoring chamber 110 and be received by the receiver 130 for determining the clean air value of the detector.

Figure 2:
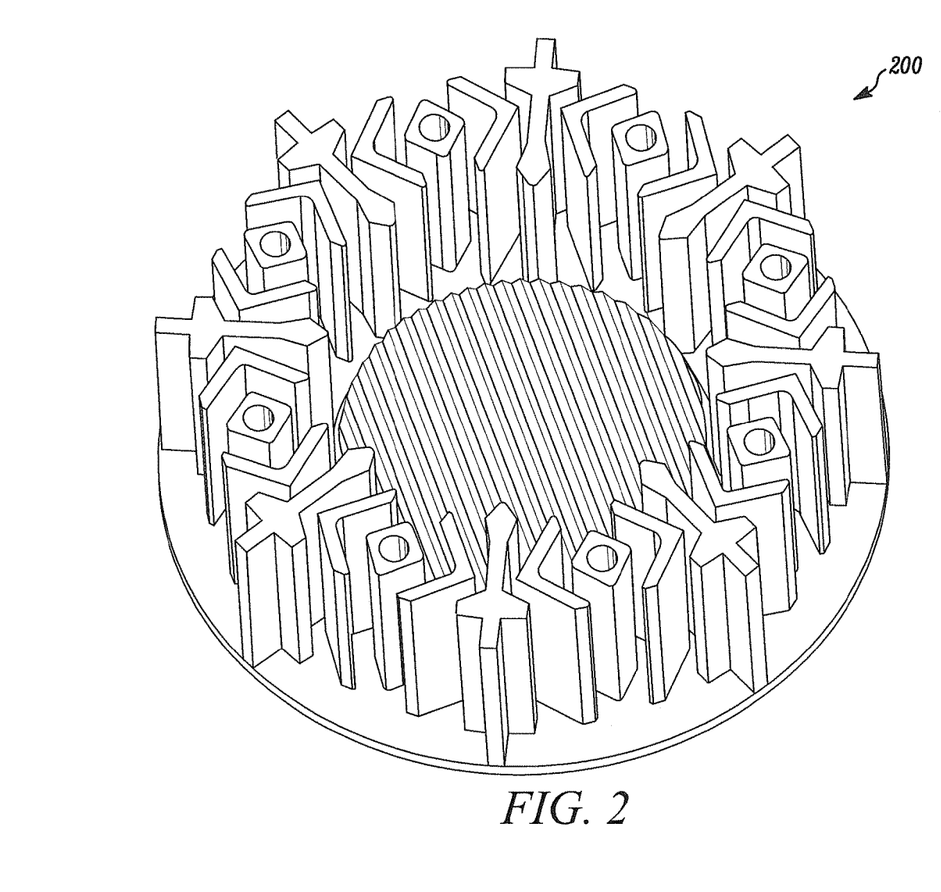
FIG. 2 is a perspective view of a first, inside side of a chamber cover in accordance with disclosed embodiments.
Figure 3:
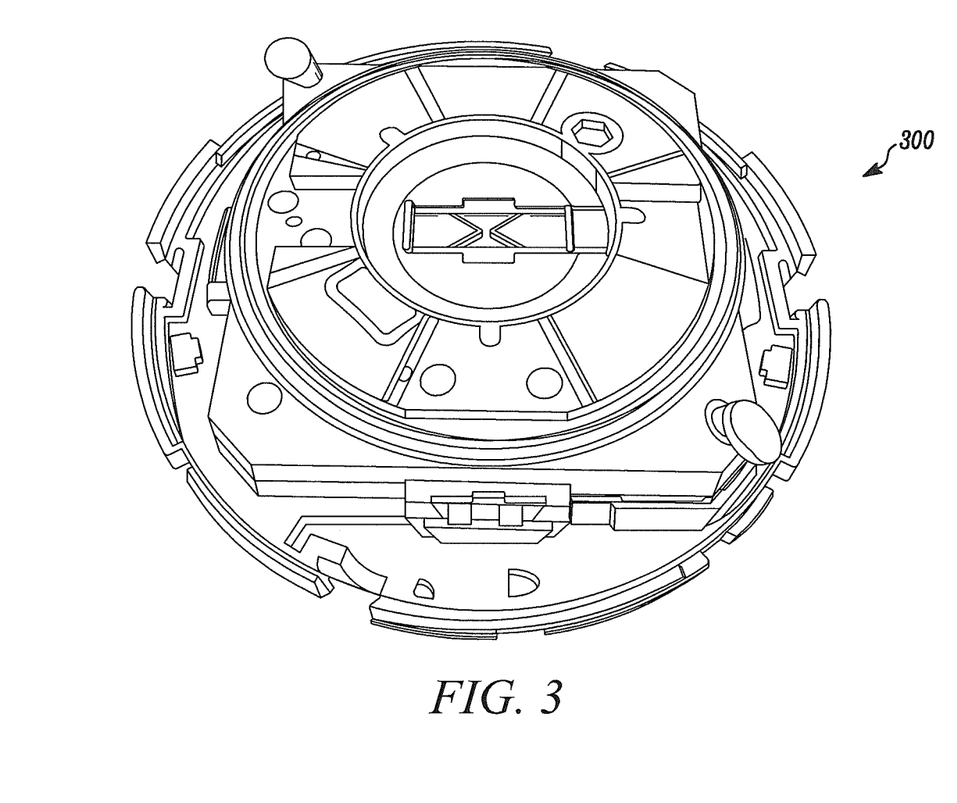
FIG. 3 is a perspective view of a first, inside side of a chamber base in accordance with disclosed embodiments.

In some embodiments, a chamber cover and a chamber base as disclosed herein can include the chamber cover and the chamber base as disclosed in U.S. application Ser. No. 14/968,136 titled "Aspirated Smoke Detector With Improved Optical Chamber". U.S. application Ser. No. 14/968,136 is assigned to the assignee hereof and is hereby incorporated by reference. For example, FIG. 2 is a perspective view of a first, inside side of a chamber cover 200 in accordance with disclosed embodiments, and FIG. 3 is a perspective view of a first, inside side of a chamber base 300 in accordance with disclosed embodiments. In some embodiments, one or both of the chamber cover and the chamber base can be realized via 3D printing, milling of known and existing chamber covers or bases, or thermoplastic molding processes.

Figure 4:
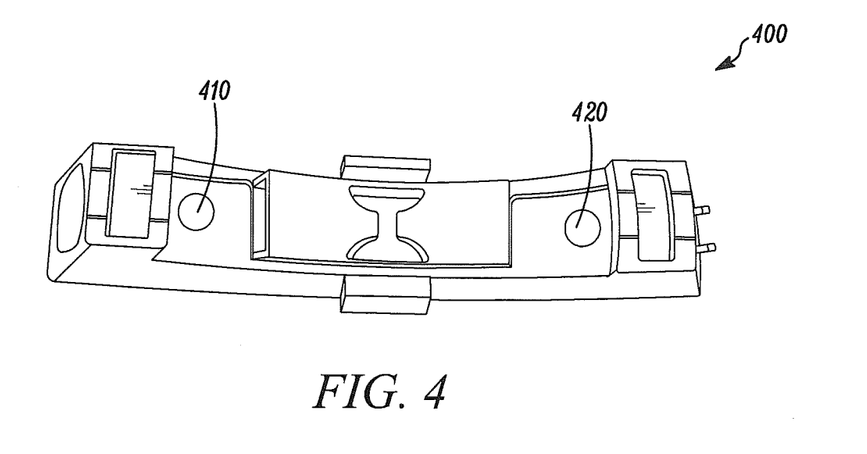
FIG. 4 is a perspective view of a first side of an optical block in accordance with disclosed embodiments.

In some embodiments, a light splitter optical block as disclosed herein can include the optical block as disclosed in U.S. application Ser. No. 14/315,646 titled "Detector With Optical Block" and in U.S. application Ser. No. 29/495,060 titled "Optical Block". Each of U.S. application Ser. No. 14/315,646 and U.S. application Ser. No. 29/495,060 is assigned to the assignee hereof and is hereby incorporated by reference. For example, the optical block as disclosed herein can include the same components and materials and be manufacturing with the same process as disclosed in either of U.S. application Ser. No. 14/315,646 and U.S. application Ser. No. 29/495,060. However, the optical block as disclosed herein can be modified to include first and second emitter and receiver holes as described herein. For example, the holes in the optical block can be manufactured and created by drilling. FIG. 4 is a perspective view of a first side of an optical block 400 in accordance with disclosed embodiments and illustrates emitter and receiver holes 410, 420 as disclosed herein.

Figure 5:
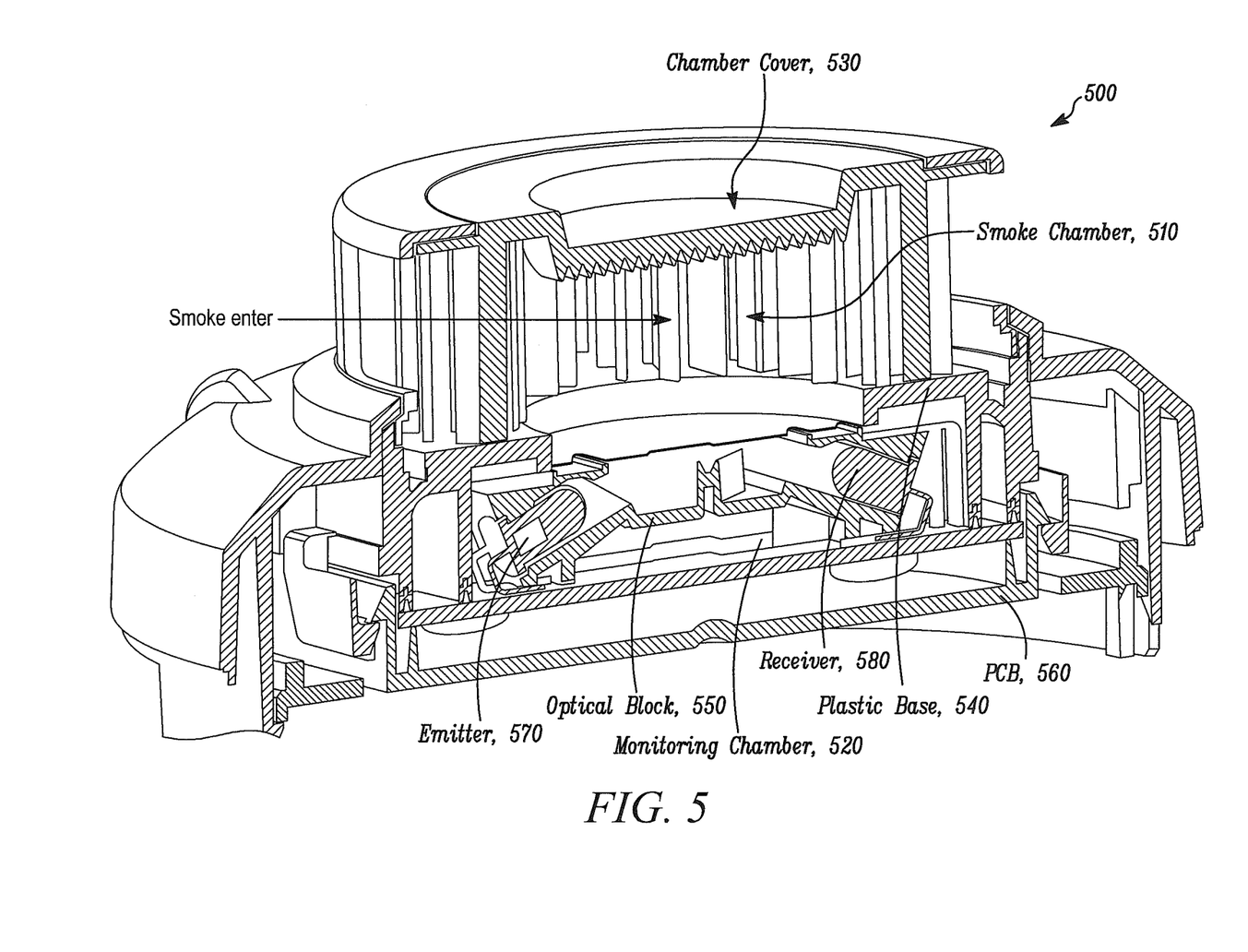
FIG. 5 is a side, cross-sectional view of a double optical chamber in accordance with disclosed embodiments.

The chamber cover, the chamber base, and the optical block as disclosed herein can be arranged relative to one another as shown in the side, cross-sectional view of a double optical chamber 500 shown in FIG. 5. As seen in FIG. 5, the double chamber 500 can include a smoke chamber 510 and a monitoring chamber 520. The smoke chamber 510 can be bounded on the top by a chamber cover 530 through which smoke can enter the smoke chamber 510 and on the bottom by a chamber base 540 and an optical block 550. The monitoring chamber 520 can be bounded on the top by the chamber base 540 and the optical block 550 and on the bottom by a PCB 560. An emitter 570 and a receiver 580 shown in FIG. 5 can emit light into the smoke chamber 510 and the monitoring chamber 520 as described above and herein and as shown in more detail in FIG. 6.

Figure 6:
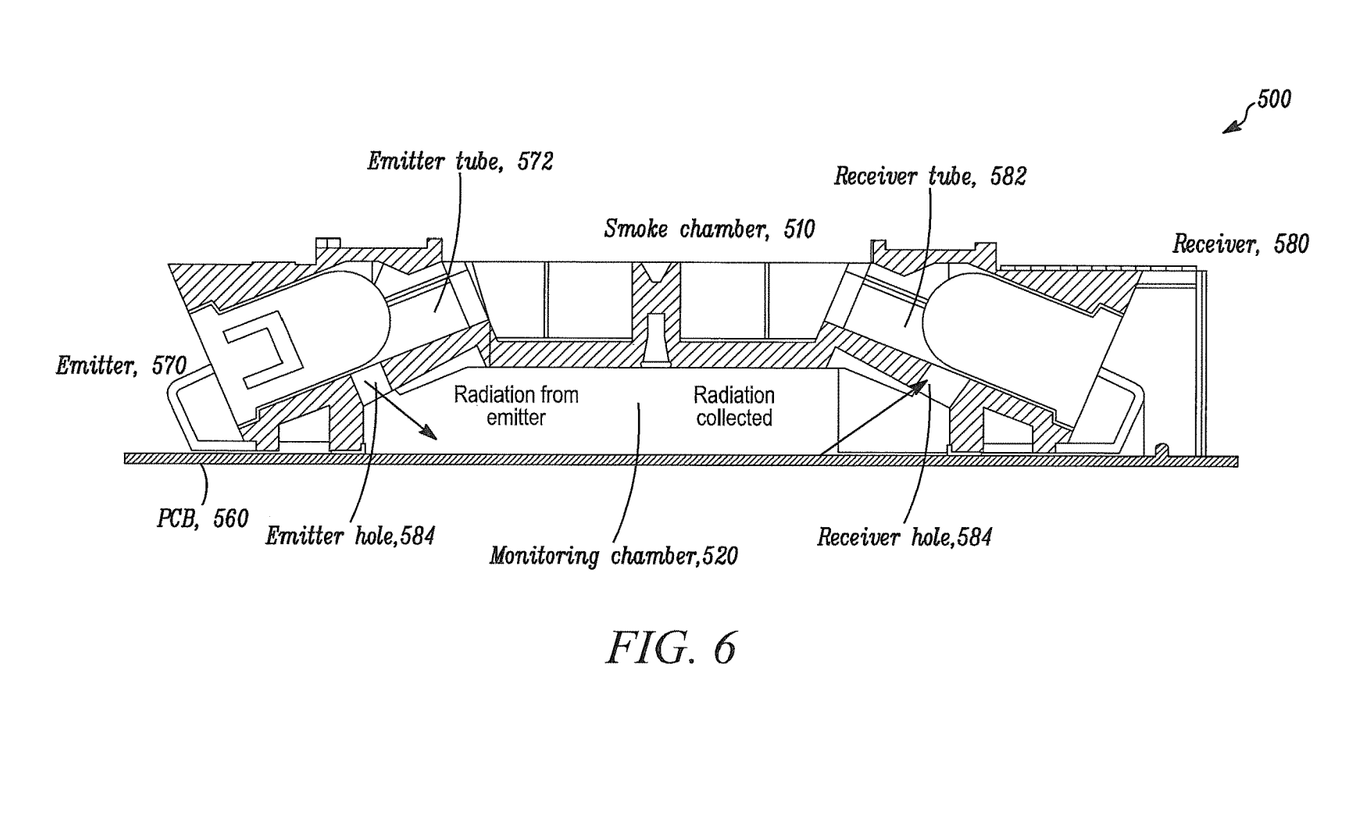
FIG. 6 is a side, cross-sectional view of a portion of the double optical chamber shown in FIG. 5.

For example, FIG. 6 is a side, cross-sectional view of a portion of the double optical chamber 500 shown in FIG. 5. As seen in FIG. 6, the emitter 570 can emit radiation into both the smoke chamber 510 and the monitoring chamber 520. A first portion of the radiation from the emitter 570 can enter the smoke chamber 510 via an emitter tube 572 in the optical block 550, and a second portion of the radiation from the emitter 570 can enter the monitoring chamber 520 via an emitter hole 574 in the optical block 550. Similarly, the radiation scattered in the smoke chamber 510 can be received by the receiver 580 via a receiver tube 582 in the optical block 550, and the radiation in the monitoring chamber 520 can be received by the receiver 580 via a receiver hole 584 in the optical block 550.

Although a few embodiments have been described in detail above, other modifications are possible. For example, the logic flows described above do not require the particular order described or sequential order to achieve desirable results. Other steps may be provided, steps may be eliminated from the described flows, and other components may be added to or removed from the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the spirit and scope of the invention.

What is claimed is:

1. A smoke detector comprising:
a chamber cover;
a chamber base;
a single emitter;
a single receiver;
an optical block; and
a printed circuit board supporting the single emitter and the single receiver,
wherein a smoke chamber is bound by the chamber cover, the chamber base, and the optical block,
wherein a monitoring chamber is bound by the chamber base, the optical block, and the printed circuit board,
wherein the monitoring chamber is closed to access outside of the smoke detector,
wherein the single emitter illuminates the smoke chamber and the monitoring chamber with light radiation,
wherein the optical block divides the light radiation into first radiation and second radiation,
wherein the first radiation includes a sensing beam that originates from a main radiation cone of the single emitter and is directed into the smoke chamber,
wherein the second radiation includes a monitoring beam that originates from one or more secondary lobes of the single emitter and is directed into the monitoring chamber,
wherein the single receiver receives the first radiation from the smoke chamber and receives the second radiation from the monitoring chamber, and
wherein the second radiation received at the single receiver from only the monitoring chamber produces a non-zero clean air value of the detector.

2. The smoke detector of claim 1, wherein the first radiation is more intense than the second radiation.

3. The smoke detector of claim 1, wherein a main view cone of the single receiver collects the sensing beam scattered in the smoke chamber.

4. The smoke detector of claim 1, wherein the optical block includes an emitter hole for passing the monitoring beam into the monitoring chamber, and wherein the emitter hole is separate from a conduit that passes the sensing beam into the smoke chamber.

5. The smoke detector of claim 4, wherein the emitter hole is fully covered by the single emitter, thereby keeping the monitoring chamber closed to the access from inside and outside of the smoke detector.

6. The smoke detector of claim 1, wherein the optical block includes a receiver hole for directing the monitoring beam from the monitoring chamber to the single receiver, and wherein the receiver hole is separate from a conduit that receives the first radiation scattered in the smoke chamber.

7. The smoke detector of claim 6, wherein the receiver hole is fully covered by the single receiver, thereby keeping the monitoring chamber closed to the access from inside and outside of the smoke detector.

8. The smoke detector of claim 1, wherein the first radiation from only the smoke chamber produces a zero clean air value.

9. The smoke detector of claim 1, wherein smoke aspirates into the smoke chamber via the chamber cover without aspirating into the monitoring chamber.

10. An optical block comprising:
an emitter housing;
an emitter tube coupled to the emitter housing for passing a first portion of radiation emitted by a main radiation cone of an emitter in the emitter housing into a smoke chamber;
an emitter hole coupled to the emitter housing and fully covered by the emitter housing for passing a second portion of the radiation emitted by one or more secondary lobes of the emitter in the emitter housing into a monitoring chamber;
a receiver housing;
a receiver tube coupled to the receiver housing for collecting and directing the first portion of the radiation scattered in the smoke chamber to a single receiver in the receiver housing; and
a receiver hole coupled to the receiver housing and fully covered by the receiver housing for collecting and directing the second portion of the radiation reflected from the monitoring chamber to the single receiver in the receiver housing,
wherein the single receiver receives the second portion of the radiation reflected from the monitoring chamber and receives the first portion of the radiation scattered in the smoke chamber,
wherein the emitter hole fully covered by the emitter housing keeps the monitoring chamber closed to outside and inside access other than the emitter and the single receiver,
wherein the receiver hole fully covered by the receiver housing keeps the monitoring chamber closed to the outside and inside access other than the emitter and the single receiver, and
wherein the radiation emitted from the emitter is divided into the first portion and the second portion.

11. The optical block of claim 10, wherein the optical block is a light splitter and a light collector.

12. The optical block of claim 10, wherein the emitter hole is disposed in a bottom surface of the emitter housing.

13. The optical block of claim 10, wherein the receiver hole is disposed in a bottom surface of the receiver housing.

14. The optical block of claim 10, wherein the first portion of the radiation is more intense than the second portion of the radiation.

15. The optical block of claim 10, wherein the receiver tube collects and directs the first portion of the radiation scattered in the smoke chamber to a main view cone of the single receiver in the receiver housing.

16. A method comprising:
providing a smoke chamber;
providing a monitoring chamber;
dividing the smoke chamber and the monitoring chamber with an optical block;
coupling a first portion of radiation from a main radiation cone of a single emitter into the smoke chamber;
coupling a second portion of the radiation from one or more secondary lobes of the single emitter into the monitoring chamber;
directing the first portion of the radiation scattered in the smoke chamber to a single receiver for collection thereof; and
directing the second portion of the radiation reflected in the monitoring chamber to the single receiver,
wherein the optical block divides the radiation from the single emitter into the first portion of the radiation and the second portion of the radiation,
wherein the monitoring chamber is closed to outside and inside access other the single emitter and the single receiver, and
wherein the second portion of the radiation collected by the single receiver from only the monitoring chamber produces a non-zero clean air value.

17. The method of claim 16, wherein the first portion of the radiation from the single emitter is coupled into the smoke chamber via a first emitter conduit, wherein the second portion of the radiation from the single emitter is coupled into the monitoring chamber via a second emitter conduit, different than the first emitter conduit, wherein the first portion of the radiation scattered in the smoke chamber is directed toward the single receiver via a first receiver conduit, and wherein the second portion of the radiation reflected in the monitoring chamber is directed toward the single receiver via a second receiver conduit, different than the first receiver conduit.

18. The method of claim 16, wherein the first portion of the radiation is more intense than the second portion of the radiation.

19. The method of claim 16 further comprising directing the first portion of the radiation scattered in the smoke chamber to a main view cone of the single receiver.

* * * * *